US00PP29998P2

(12) United States Plant Patent
Stemkens

(10) Patent No.: US PP29,998 P2
(45) Date of Patent: Dec. 18, 2018

(54) ***VERBENA* PLANT NAMED 'VEAZ0047'**

(50) Latin Name: *Verbena hybrida*
Varietal Denomination: VEAZ0047

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,418

(22) Filed: Jun. 6, 2017

(51) Int. Cl.
*A01H 5/02* (2018.01)

(52) U.S. Cl.
USPC ..... Plt./308
CPC ..... *A01H 5/02* (2013.01)

(58) Field of Classification Search
USPC ..... Plt./308
CPC ..... A01H 5/02
See application file for complete search history.

*Primary Examiner* — Kent L Bell
(74) *Attorney, Agent, or Firm* — Dale Skalla

(57) ABSTRACT

A new *Verbena* plant named 'VEAZ0047' particularly distinguished by the large sized inflorescences, flowers having 2 upper petals dark pink and 3 lower petals pink, medium green, undivided leaves, and a semi-upright plant habit.

1 Drawing Sheet

Latin name of the genus and species of the plant claimed: *Verbena hybrida.*

Varietal denomination: 'VEAZ0047'.

BACKGROUND OF THE NEW PLANT

The present invention comprises a new *Verbena*, botanically known as *Verbena hybrida*, and hereinafter referred to by the variety name 'VEAZ0047'.

'VEAZ0047' is a product of a planned breeding program. The new cultivar has large sized inflorescences, flowers with 2 upper petals being dark pink and 3 lower petals being pink, medium green, un-divided leaves and a semi-upright plant habit.

'VEAZ0047' originated as a naturally occurring branch mutation found in July 2011 in a greenhouse in Enkhuizen, The Netherlands. The female parent plant was 'J0966-1' having a bright rose color and smaller flowers.

'VEAZ0047' was selected as one flowering cutting of the stated plant in July 2011 and immediately reproduced.

Therefor the first act of asexual reproduction of 'VEAZ0047' was accomplished when vegetative cuttings were propagated in July 2011 in a greenhouse in Enkhuizen, The Netherlands.

BRIEF SUMMARY OF INVENTION

Horticultural examination of plants grown from cuttings of 'VEAZ0047' initiated in the fall of 2011, and continuing thereafter, has demonstrated that the combination of characteristics as herein disclosed for 'VEAZ0047' are firmly fixed and are retained through successive generations of asexual reproduction.

'VEAZ0047' has not been observed under all possible environmental conditions. The phenotype may vary significantly with variations in environment such as temperature, light intensity, and day length.

A Plant Breeder's Right for this cultivar has not been applied for. 'VEAZ0047' has not been made publicly available prior to the effective filing date of this application, notwithstanding any disclosure that may have been made less than one year prior to the effective filing date of this application by the inventor or another who obtained 'VEAZ0047' directly from the inventor.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawings show typical flower and foliage characteristics of 'VEAZ0047' with colors being as true as possible with an illustration of this type.

Figure 1:
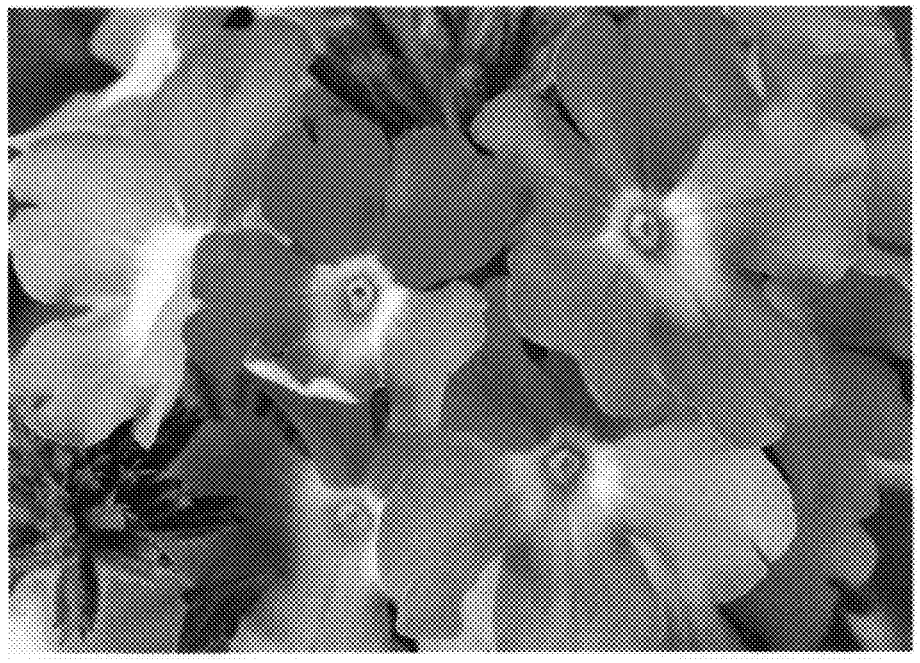
Figure 2:
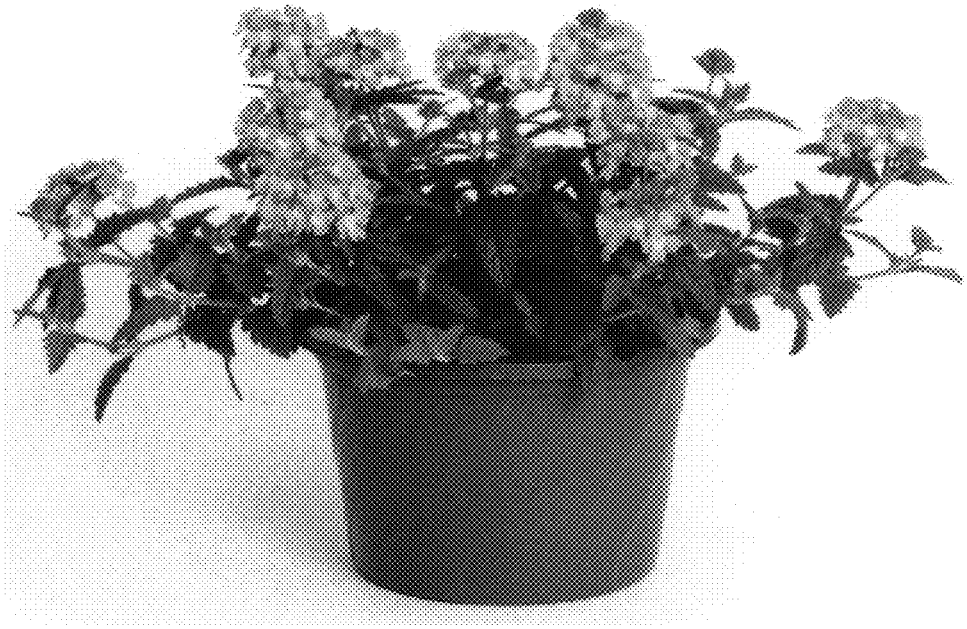

The photographic drawing in FIG. 1 shows a close up view of an inflorescence of the new plant, and in FIG. 2 a whole flowering plant. The aforementioned photographs were taken in July 2016 in Andijk, The Netherlands. The plants were about 12 weeks old and were grown in 12 cm pots.

DETAILED BOTANICAL DESCRIPTION

The measurement were taken in July 2016 in Andijk, The Netherlands. The plants were about 12 weeks old and were grown in 12 cm pots.

Color references are made to The Royal Horticultural Society Colour Chart (R.H.S.) 2001.

TABLE 1

DIFFERENCES BETWEEN THE NEW VARIETY 'VEAZ0047' AND A MOST SIMILAR VARIETY

| | 'VEAZ0047' | 'Lanai Bright Pink' (U.S. Plant Pat. No. 13,982) |
|---|---|---|
| Flower color: | Upper petals darker, lower petals lighter | All petals same color |

TABLE 1-continued

DIFFERENCES BETWEEN THE NEW VARIETY 'VEAZ0047' AND A MOST SIMILAR VARIETY

| | 'VEAZ0047' | 'Lanai Bright Pink' (U.S. Plant Pat. No. 13,982) |
|---|---|---|
| Flower, size: | Larger | Smaller |
| Leaf, size: | Medium | Small |
| Leaf incision: | Entire | Dentate |

Plant:

*Form, growth and habit.*—Herbaceous, semi upright and free branching.

*Plant height.*—16.0 cm.

*Plant height (inflorescence included).*—20.0 cm.

*Plant width.*—39.0 cm.

Roots:

*Number of days to initiate and produce roots.*—11-13 days at about 23 degrees C.

*Type.*—Fine, fibrous, free branching.

*Color.*—RHS N155B but whiter.

Foliage:

*Arrangement.*—Opposite, simple.

*Immature, leaf color, upper surface.*—RHS 138B.

*Immature, leaf color, lower surface.*—RHS 138C.

*Mature, leaf color, upper surface.*—RHS 138A.

*Mature, leaf color, lower surface.*—RHS 137D.

*Length.*—Approximately 2.8 cm.

*Width.*—3-3.2 cm.

*Shape.*—Hastate.

*Base shape.*—Rounded or obtuse.

*Apex shape.*—Obtuse.

*Margin.*—Entire.

*Texture, upper surface.*—Pubescent.

*Lower surface.*—Pubescent.

*Color of veins, upper surface.*—RHS 145B.

*Color of veins, lower surface.*—RHS 145A.

*Pattern of veining.*—Pinnate.

*Petiole color.*—RHS 145B.

*Petiole length.*—0.6 cm.

*Petiole width.*—0.4 cm.

*Texture.*—Hirsute.

Stem:

*Branching characteristics.*—Side branches develop potentially at each node.

*Quantity of main branches per plant.*—12-15.

*Color of stem.*—RHS 143A.

*Stem length.*—About 21.0-32.0 cm.

*Stem width.*—About 0.28 cm.

*Length of internodes.*—About 2 to 3.3 cm.

*Texture.*—Hirsute.

*Color of peduncle.*—RHS 138C.

*Length of peduncle.*—From 2.8 to 4.5 cm.

*Peduncle diameter.*—0.2 cm.

*Texture.*—Glandular hairs.

Inflorescence:

*Type.*—Umbel-like, but actually a spike, umbrella-shaped.

*Blooming habit.*—Flowers continuously during the summer months.

*Lastingness of individual blooms on the plant.*—About 3-4 days in the greenhouse.

*Fragrance.*—None.

*Number of inflorescences per plant.*—48 at various stages at development.

*Horizontal diameter of inflorescence.*—6.4-6.9 cm.

*Depth of inflorescence.*—3.9 cm.

*Number of florets and buds per inflorescence.*—Approximately 35-37.

Bud:

*Color.*—RHS N155B.

*Length.*—0.3 cm (future corolla only).

*Width.*—0.25 cm.

*Shape.*—Tubular with bulbous apex.

Floret:

*Form.*—Sessile; salver-shaped, composed of 5 partly fused petals with a base of a narrow tube.

Immature color, upper surface:

2 *upper petals.*—RHS N57C and lower part of 0.3 mm RHS 155C.

3 *lower petals.*—RHS 58D and lower part of 0.3 mm RHS 155C.

Immature color, lower surface:

2 *upper petals.*—RHS 69A.

3 *lower petals.*—RHS 69C.

Mature color, upper surface:

2 *upper petals.*—RHS N57D and lower part of 0.3 mm RHS 155C.

3 *lower petals.*—RHS 62A and lower part of 0.3 mm RHS 155C.

Mature color, lower surface:

2 *upper petals.*—RHS 69C.

3 *lower petals.*—RHS 69D.

*Floret diameter.*—4.8 cm.

*Floret length (depth).*—3.8 cm.

*Petal length.*—1.6 cm.

*Petal width.*—1.5 cm.

*Shape.*—Obcordate.

*Apex shape.*—Emarginate.

*Margin.*—Entire.

*Petal texture, upper surface.*—Papillose; a little glandular hair.

*Petal texture, lower surface.*—Papillose, pubescent.

*Corolla tube length.*—2.7 cm.

*Corolla tube width.*—0.2 cm.

*Corolla tube color inside.*—RHS 69C.

*Tube color outside.*—RHS 69D.

*Corolla texture, inside.*—Pubescent.

*Corolla texture, outside.*—Canescent.

*Throat hair color.*—RHS 155C but whiter.

Calyx:

*Type.*—Five sepals whose margins are fused to each other along their length, with a transparent membrane of less than 0.1 cm in width and with one smaller sepal attached to the base of the calyx.

*Color of lower sepal surface.*—RHS 143B.

*Length of sepals.*—1.2 cm.

*Width of sepals.*—0.2 cm.

*Sepal shape.*—Fused, linear.

*Apex shape.*—Acute.

*Margins.*—Entire.

*Texture.*—Densely covered with very short glandular hair.

Reproductive organs:

Gynoecium:

*Pistil.*—1.

*Pistil length.*—1.6 cm.

*Style color*.—RHS N144B.
*Style length*.—1.6 cm.
*Stigma color*.—RHS 144A.
*Ovary color*.—RHS 144B.
*Ovary length*.—0.2 cm.
*Ovary width*.—0.1 cm.

Androecium:

*Stamens*.—Anthers and filaments fused to upper half of corolla tube; four anthers with two pollen sacs per anther.
*Color of filaments*.—RHS 151D.
*Filament length*.—0.2 cm.
*Anther color*.—RHS 151C.
*Anther length*.—0.1 cm.
*Pollen amount*.—None observed.

Fertility/seed set: Neither seed nor fruit production has been observed.

Disease/pest resistance: Resistance to pathogens and pests common to *Verbena* has not been observed.

What is claimed is:

1. A new and distinct variety of *Verbena* plant named 'VEAZ0047' substantially as illustrated and described herein.

* * * * *